United States Patent [19]
Hadlaczky

[11] Patent Number: 5,288,625
[45] Date of Patent: Feb. 22, 1994

[54] MAMMALIAN ARTIFICIAL CHROMOSOMES

[75] Inventor: Gyula Hadlaczky, Szamos, Hungary

[73] Assignee: Biologic Research Center of the Hungarian Academy of Sciences, Hungary

[21] Appl. No.: 759,558

[22] Filed: Sep. 13, 1991

[51] Int. Cl.$^5$ .................. C12N 15/06; C12N 15/12; C12N 5/16; C12N 5/28
[52] U.S. Cl. .................. 435/172.2; 435/172.3; 435/240.2; 435/240.26
[58] Field of Search ............... 435/240.2, 172.3, 172.2, 435/320.1, 240.26

[56] References Cited

U.S. PATENT DOCUMENTS

| 4,608,339 | 8/1986 | Yoakum et al. | 435/172.2 |
| 4,935,350 | 6/1990 | Patel et al. | 435/69.4 |
| 4,970,162 | 11/1990 | Aksamit | 435/240.26 |

OTHER PUBLICATIONS

Richa et al., Science, vol. 245, 1989, pp. 175–177.
Frohman et al., Cell, vol. 56, 1989, pp. 145–147.
Willard et al., Trends in Genetics, vol. 3, 1987, pp. 192–198.
Blackburn, et al., Ann. Rev. Biochem., vol. 53, pp. 163–194, 1984.
Bower, Eur. Cong. Biotechnol., vol. 3, p. 571, 1987, abstract.
Burke, et al., Science, vol. 236, pp. 806–812, 1987.
Carine, et al., Somatic Cell and Molecular Genetics, vol. 12, pp. 479–491, 1986.
Clarke, et al., Ann. Rev. Genet., vol. 19, pp. 29–56, 1985.
Murray, et al., Nature, vol. 305, pp. 189–193, 1983.
Solus, et al., Somatic Cell and Molecular Genetics, vol. 14, pp. 381–391, 1988.

*Primary Examiner*—Richard A. Schwartz
*Assistant Examiner*—James Ketter
*Attorney, Agent, or Firm*—Banner, Birch, McKie & Beckett

[57] ABSTRACT

Non-human cell lines are disclosed which contain functional centromeres comprising human DNA sequences linked to a dominant marker gene. The centromeres are carried on stable chromosomes which carry no centromeres other than those comprising human DNA sequences. The cell lines can be used to isolate the chromosomes as well as for use in inserting genes into mammalian cells. Methods are taught for generating such cell lines from cell lines carrying dicentric chromosomes.

12 Claims, 3 Drawing Sheets

MAMMALIAN ARTIFICIAL CHROMOSOMES

BACKGROUND OF THE INVENTION

The centromere is a specialized region of the eukaryotic chromosome. It is the site of kinetochore formation, a structure which allows the precise segregation of chromosomes during cell division. In addition to this, a possible structural role in the higher-order organization of eukaryotic chromosomes has also been suggested (Hadlaczky (1985), Internatl. Rev., 94:57-76).

The isolation and cloning of centromeres is crucial, not only to understanding their molecular structure and function, but also for the construction of stable artificial chromosomes. Taking advantage of the existence of centromere-linked genes, functional centromeres of lower eukaryotes (yeast) have been successfully isolated (Blackburn, et al. (1984) Ann. Rev. Biochem., 53:163-194; Clarke, et al. (1985), Ann. Rev. Genet., 19:29-56). The combination of a functional centromere with telomeres, which stabilize the chromosome ends, permitted the construction of yeast artificial chromosomes (Murray, et al. (1983) Nature, 305:189-193; Burke, et al. (1987), Science, 236:806-812). This initiated a new era in the study of chromosome function and in genetic manipulation.

Higher eukaryotes (e.g., mammals), in contrast to yeast, contain repetitive DNA sequences which form a boundary at both sides of the centromere. This highly repetitive DNA interacting with certain proteins, especially in animal chromosomes, creates a genetically inactive zone (heterochromatin) around the centromere. This pericentric heterochromatin keeps any selectable marker gene at a considerable distance, and thus repetitive DNA prevents the isolation of centromeric sequences by chromosome "walking."

Thus there is a need in the art for mammalian artificial chromosomes. Use of such chromosomes could overcome problems inherent in present techniques for introduction of genes into mammalian cells, including the concomitant creation of insertional mutations, size limitations on introduced DNA, and imperfect segregation of plasmid vectors.

SUMMARY OF THE INVENTION

It is an object of the present invention to provide a cell line which can be used as a source of mammalian artificial chromosomes.

It is another object of the invention to provide a method for producing a cell line which comprises a functioning centromere comprising human DNA sequences, wherein the centromere is present on a chromosome, wherein all of the centromeres of said chromosome comprise human sequences linked to a dominant selectable marker.

These and other objects are provided by one or more of the embodiments described below.

In one embodiment of the present invention a non-human cell line is provided which comprises a functioning centromere comprising human DNA sequences, wherein the centromere is present on a chromosome and wherein all of the centromeres of said chromosome comprise human sequences linked to a dominant selectable marker.

In another embodiment a method is provided for producing a cell line which comprises a functioning centromere comprising human DNA sequences, wherein the centromere is present on a chromosome, wherein all of the centromeres of said chromosome comprise human sequences linked to a dominant selectable marker, comprising:

growing cells of a cell line deposited at the European Collection of Animal Cell Culture (ECACC) under accession no. 90051001 in a culture medium comprising a selective agent for the dominant selectable marker, said selective agent present in the culture medium in an amount greater than ten times the amount which kills 50% of the cells;

selecting cells which survive in said culture medium;

screening the surviving cells or their progeny for cells which are devoid of a dicentric chromosome.

In yet another embodiment of the invention a method is provided for producing a cell line which comprises a functioning centromere comprising human DNA sequences, wherein the centromere is present on a chromosome, wherein all of the centromeres of said chromosome comprise human sequences, comprising:

fusing cells of the cell line deposited at the European Collection of Animal Cell Culture (ECACC) under accession no. 90051001 with cells of a second mammalian species to form fused cell hybrids;

screening said fused cell hybrids or their progeny for cells which are devoid of a dicentric chromosome but which contain a centromere which comprises human DNA.

These and other embodiments will be described in more detail below. The present invention thus provides the art with cell lines which can be used as sources of mammalian artificial chromosomes. The artificial chromosomes can be stably maintained in cell lines and can be isolated for use as vectors for desired genetic elements.

BRIEF DESCRIPTION OF THE DRAWINGS

FIG. 1 shows immunostaining of KE1 2/4 cells with anti-centromere antibodies and in situ hybridization of KE1 2/4 and EC3/7 cells with biotin-labelled DNA probes. Chromosomes were counterstained with propidium iodide.

FIG. 2 shows the structure of the Hoechst dye 33258-treated λneo chromosome; a to g are the individual amplicons.

FIG. 3 shows centromere detection of KE1 2/4 chromosomes by immunostaining and double in situ hybridization. The chromosomes were counterstained with propidium iodide.

DETAILED DESCRIPTION

Figure 1A:
FIG. 1A: Indirect immunofluorescence staining of KE1 2/4 metaphase chromosomes with anti-centromere serum (LU851).

It is the discovery of the present invention that a cell line which contains a dicentric chromosome, one of the centromeres of which contains a segment of human DNA, can be treated so as to isolate the centromere which contains the human DNA on a chromosome away from other mammalian centromeres. This conclusively demonstrates that the centromere which contains human DNA is a functional centromere.

The functional centromeres containing human DNA are obtained from a cell line deposited at the European Collection of Animal Cell Cultures (ECACC) Porton Down, U.K. under Accession No. 90051001, on May 10, 1990, under the conditions of the Budapest Treaty, also known as EC3/7. This cell line is a mouse lung fibroblast cell line which contains a dicentric chromosome, one of the centromeres of which contains human DNA sequences. The centromere which can be isolated from this cell line is linked to a dominant selectable marker, the aminoglycoside-3' phosphotransferase-II which provides resistance to G418 (Sigma). Cells of line EC3/7 are relatively heterogeneous, carrying either a dicentric (85%) or a minichromosome (10%). Centromeres of dicentric chromosomes and minichromosomes were indistinguishable from the normal mouse centromeres by immunostaining with anticentromere antibodies. The cells carrying minichromosomes could not be stably cloned by single cell cloning. Prior to the present invention, the minichromosomes had not been found stably maintained. The present invention provides derivative cell lines which stably replicate a chromosome which contains only centromeres comprising cloned human DNA.

Two such derivatives are provided by the present invention. One derivative cell is a mouse-hamster hybrid cell line which was formed by fusing EC3/7 with a Chinese hamster ovary (CHO) cell. Applicants have found that upon or subsequent to formation of the hybrid cell line, amplification of the human-derived centromere occurred. The amplification resulted in a chromosome which contained no purely rodent centromeres, although it was the size of a rodent chromosome. The amplified centromere (referred to herein as λneo) was present seven times in most cells (see Table I). Only one of the amplified centromeres appears to be functional in the cells.

A second derivative cell carries a stable minichromosome comprising a human DNA-containing centromere derived from EC3/7. A minichromosome is less than half the size of the smallest chromosome in a cell line. A stable minichromosome can be formed by growing cells containing dicentric chromosomes, such as EC3/7, in high levels of selective agents, which leads to amplification of the selectable marker as well as linked sequences. For example, if 10 μg/ml of an antibiotic such as G418 is the lethal dose (i.e., prevents $10^6$ cells from surviving for 3 weeks), 400 μg/ml can be used to select for amplification. Generally, at least ten times, and more preferably twenty to forty times, the dosage which kills $10^6$ cells is desirable. Selection of EC3/7 cells on 400 μg/ml G418 led to formation of cells carrying stable minichromosomes, rather than dicentric chromosomes. Screening for loss of dicentric chromosomes can be done by standard cytogenetic techniques, as well as by immunostaining with anti-centromere antibodies.

Stable maintenance of chromosomes, according to the present invention occurs when at least 90% of cells of a cell-line retain the chromosome. Preferably 95% of the cells retain the chromosome. Stability is measured in the presence of selective agent. Preferably these chromosomes are also maintained in the absence of a selective agent. Stable chromosomes also retain their structure during cell culturing, suffering neither intrachromosomal nor interchromosomal rearrangements.

Minichromosomes can be physically isolated from mitotic cells of the cell lines which stably carry them. They can be partially purified by differential centrifugation followed by sucrose gradient sedimentation. Such a method yields preparations which are about 10–20% minichromosomes.

Minichromosomes (or their amplified derivatives) can be used as vectors in chromosome-mediated gene transfer. Mammalian cells can be transfected with minichromosomes, or genetically engineered minichromosomes, using calcium phosphate, liposomes, electroporation, or any method known in the art. The minichromosomes can be used to microinject eggs, embryos or cultured cells. Minichromosome-containing cells can also be used to fuse to human stem cells or bone marrow cells. Other applications will be clear to those of skill in the art.

The following examples do not limit the invention to the particular embodiments described, but are presented to particularly describe certain ways in which the invention may be practiced.

EXAMPLE 1

This example describes the stability of the EC3/7 cell line.

Forty-six independent subclones derived from a single cell were isolated and analyzed. Each of the subclones carried the dicentric chromosome. The percentage of minichromosome-containing cells varied between 2% and 30% in different subclones. We were unable to isolate a subclone by single cell subcloning which carried the additional centromere exclusively in a minichromosome. This result suggests that the minichromosomes are unstable and they can be regarded as the products of regular breakages of the dicentric chromosomes.

By subcloning the EC3/7 cell line in high concentrations of G418 (forty-fold the lethal dose) for 350 generations, two single cell-derived stable cell lines (EC3/7C5 and EC3/7C6) were established which carried the extra centromere solely on minichromosomes. Indirect immunofluorescence with anti-centromere antibodies and subsequent in situ hybridization experiments proved that the minichromosomes derived from the dicentric chromosome. In both cell lines the majority of the hybridization signal was found on the minichromosomes but traces of CM8 or lambda sequences were detected at the end of a monocentric chromosome. In EC3/7C5 and EC3/7C6 cell lines (140 and 128 metaphases, respectively) no dicentric chromosomes was found and minichromosomes were detected in 97.2% and 98.1% of the cells, respectively. The minichromosomes are maintained for over 150 cell generations. Multiple copies of telomeric DNA sequences were detected in the marker centromeric region of the dicentric chromosome by in situ hybridization. This indicates that mouse telomeric sequences were coamplified with the foreign DNA sequences. These stable minichromosome-carrying cell lines provide direct evidence that the extra centromere containing human sequences is functioning and is capable of maintaining the minichromosomes.

A preliminary analysis by immunostaining of EC3/7 cells (103 metaphases) cultured for 46 days in non-selective medium showed that 80.6% of the cells contained either a dicentric (60.2%) or a minichromosome (20.4%). Subsequent in situ hybridization with biotin-labelled probes proved the presence of the "foreign" DNA in the additional centromere. These results indicate that no serious loss or inactivation of the additional centromeres had occurred during this period of culture under non-selective conditions.

EXAMPLE 2

This example demonstrates the inter-specific fusion of EC3/7 mouse cells and the formation of a stable chromosome carrying human sequences.

EC3/7 mouse fibroblast cell line was grown as a monolayer in F12 medium supplemented with 10% fetal calf serum (FCS) and 400 µg/ml G418 (Geneticin, SIGMA). Chinese Hamster Ovary cells (CHO K-20) were grown in F12 medium supplemented with 10% FCS. $1.8 \times 10^7$ CHO cells and $2.3 \times 10^6$ EC3/7 cells were fused using polyethylene glycol (Davidson, Som. Cell Genet., vol. 2, pp. 165-176 (1976)). Hybrids were selected and maintained in F12 HAT medium (Szybalski, N.C.I. Monogr., vol. 7, pp. 75-89 (1982)) containing 10% FCS and 400 µg/ml G418.

Figure 1B:
FIG. 1B: The same metaphase after subsequent in situ hybridization with biotinylated lambda DNA probe.
Figure 1C:
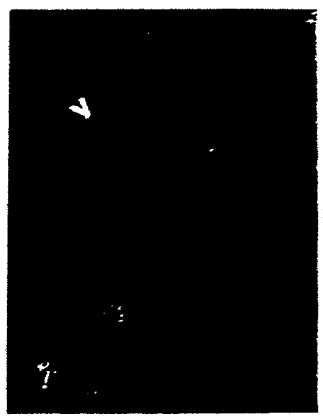
FIG. 1C: In situ hybridization with neo.

Several hybrid cell lines were obtained by the fusion of LMTK− EC3/7 mouse cells with CHO K-20 hamster cells. The EC3/7 cells carried a functional marker centromere linked to a dominant selectable gene (neo) in the majority of the cells on a dicentric chromosome or less frequently (10%) on a minichromosome. Hybrids were selected and maintained on HAT medium containing 400 µg/ml G418 (Geneticin, Sigma). During the cytological analysis of independent hybrid lines, the neo-linked marker centromere was monitored by indirect immunofluorescence staining with human anti-centromere serum (LU851) and by subsequent in situ hybridization using a biotin-labelled λ DNA probe, as described above. Nine hybrid clones carried the dicentric chromosome with the extra marker centromere. In one hybrid line (KE1 2/4), at the $10^7$ cell stage (65 days after fusion), the marker centromere departed from the dicentric chromosome, and a new chromosome was formed, which had the size of an average mouse chromosome (FIG. 1A). In situ hybridization with a biotin-labelled λ probe showed an intense hybridization signal on the newly formed (λneo) chromosome (FIG. 1B). The results of in situ hybridizations on the λneo chromosome clearly indicate that this chromosome was derived from the marker centromere region (that carrying neo sequences) of the dicentric chromosome.

The λneo chromosome was found to be quite stable in this cell line. In a 65 day culture ($10^7$ cell stage), 92 out of the 96 metaphases analyzed showed the presence of the λneo chromosome. Three metaphases showed translocations of λneo chromosome segments, and in 1 metaphase this chromosome was not detectable at all. In 110 day cultures, more than 98% of the cells (167 metaphases analyzed) carried a λneo chromosome. When KE1 2/4 cells were cultured for an additional 43 days (>50 generations) under non-selective conditions (HAT−, G418−), 84.4% of the cells (96 metaphases analyzed) retained the λneo chromosome.

EXAMPLE 3

This example describes the characteristics of the λneo chromosomes.

In situ hybridizations with biotin-labelled probes were carried out as described (Graham, et al., Virology, vol. 52, pp. 456-467, 1973). Double in situ hybridizations were carried out as follows. After the first hybridization, metaphases were photographed, the coverslips were removed and slides were rinsed in PBS. Wet slides were denatured in 70% formamide (BDH AnalaR)/2×SSC at 72° C. for 5 min., and a standard hybridization procedure (Graham, supra) was followed using a second biotin-labelled probe. In situ hybridization experiments indicate the presence of interspersed neo (FIG. 1B), and human (FIG. 1H) DNA sequences. This finding suggests that the λneo chromosome was formed by an extensive amplification process. Neither conventional cytology nor in situ hybridization detected extrachromosomal structures in the KE1 2/4 cell line.

Figure 1D:
FIG. 1D: Telomere probes, arrowheads indicate λneo chromosomes.
Figure 1E:
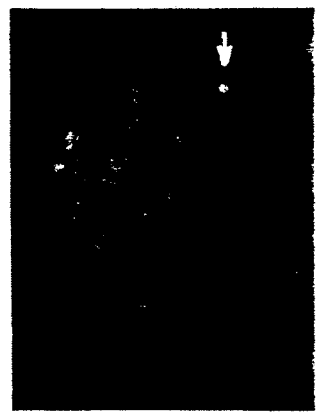
FIG. 1E: In situ hybridization of EC3/7 metaphase with telomere probe. The arrow shows the dicentric chromosome.

Since telomeres are thought to be necessary for chromosome stability, the question arose whether telomeric sequences were present in the λneo chromosome. To answer this question, in situ hybridizations were carried out with a telomeric repeat $(TTAGGG)_n$ sequences, which is common in vertebrate species (Meyne, et al., Chromosoma, vol. 99, pp. 3-10, 1990). Sequences which hybridize to telomeric sequences were found to be scattered throughout the entire λneo chromosome (FIG. 1D). In addition, heavy labeling was detected over the pericentric regions of some hamster chromosomes that are enriched in TTAGGG repeats (Meyne, et al., supra). Hybridizations on "parental" EC3/7 metaphases revealed the origin of the TTAGGG repeats. The entire distal centromeric region of the dicentric chromosome, where the marker centromere was located, showed an intense hybridization signal with a biotin-labelled telomere probe (FIG. 1E). This suggests that during the initial amplification when the marker centromere region of the dicentric chromosome was formed, telomeric sequences coamplified with the human (λCM8) and neo (λgtWESneo) sequences.

Figure 1F:
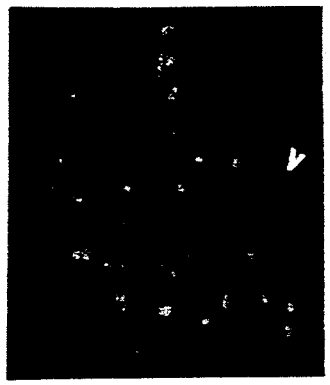
FIG. 1F: In situ hybridization of KE1 2/4 chromosomes with total mouse DNA probe showing preferential label on the pericentric regions of mouse chromosomes, and banded pattern on the λneo chromosome (arrowhead).

To test whether other repetitive sequences participated in the formation of the λneo chromosome, biotin-labelled total mouse and hamster DNA probes were used for in situ hybridizations. No signal was found on the λneo chromosome with the total hamster DNA probe. Using the mouse probe, the pericentromeric regions of the mouse chromosomes showed an intense hybridization, and a distinct hybridization pattern was detected on the λneo chromosome. Regular narrow bands were observed along the λneo chromosome (FIG. 1F). These results indicate that the breakage, which separated the marker centromere from the dicentric chromosome, occurred in the pericentric region of the adjacent mouse centromere. During the amplification process that led to the formation of the λneo chromosome, this repetitive mouse DNA bordered the large (>10 Mb) amplicons (amplified units).

When mouse fibroblast cells are cultured in the presence of the DNA-binding dye Hoechst 33258, a prominent undercondensation of the pericentric heterochromatin of the metaphase chromosomes occurs (Hilwig, et al., *Exp. Cell Res.*, vol. 81, pp. 474–477 (1973)). Using this technique on the KE1 2/4 cell line we expected to observe a longitudinal segmentation of the λneo chromosome. We hoped this would provide finer details of the chromosome substructure than revealed by the in situ hybridization produced on condensed chromosomes (FIG. 1F).

Figure 1G:
FIG. 1G: Carbol-fuchsin stained metaphase of Hoechst dye 33258-treated KE1 2/4 chromosomes.

Hoechst dye 33258-treated λneo chromosomes showed a regular undercondensation of the regions corresponding to the hybridizing bands of mouse repetitive sequences (FIG. 1G) which suggests that they have a pericentromeric origin. It was previously reported that the main DNA component of mouse pericentric heterochromatin is the major satellite DNA (Wong, et al., *Nucl. Acids. Res.*, vol. 16, pp. 11645–11661 (1988)). The in situ hybridization pattern with a biotin-labelled mouse major satellite probe (kindly provided by Dr. J. B. Rattner) was indistinguishable from the pattern detected by the total mouse DNA probe (FIG. 1F) indicating that amplicon borders are enriched in mouse major satellite DNA sequences and behave as mouse pericentric heterochromatin.

The Hoechst dye 33258-induced undercondensation of certain regions of λneo chromosomes also made it possible to reveal detailed structural features of this chromosome:

1. The number of amplicons, first detected at the $10^7$ cell stage (65 days in culture), showed a certain degree of consistency. In 65.6% of the cells, the number of amplicons was found to be 7. This consistency in the number of amplicons was slightly increased (73.2% of 1500 metaphases analyzed) after 110 day culture, and was maintained under non-selective culture conditions (43 days). In the 254 day culture the number λneo chromosomes with 7 amplicons reached 80% (Table 1).

Figure 2A:
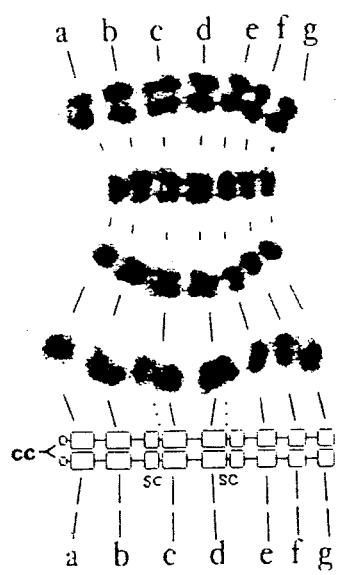
FIG. 2A: The "amplicon map" of λneo chromosomes from four different metaphases. On the schematic drawing the position of the centromere is shown by cc, "secondary constrictions" of c and d amplicons are marked by sc symbols.

2. The amplicons of a given λneo chromosome were of different sizes, but the size of a given amplicon remained constant in different cells. This finding made it possible to "map" the λneo chromosome: two similar sized blocks (a,b) and two large units (c,d) followed by three small amplicons (e,f, and g) completed the chromosome (FIG. 2A).

3. The presence of a small amount of mouse major satellite sequences within the amplicons can produce "secondary constrictions" (sc) therefore it is possible to visualize finer structural details of the well spread elongated chromosomes. Secondary constrictions divided the c,d units into unequal parts, and a mirror symmetry of these amplicons was observed (FIG. 2A), which suggested an inverted orientation of the c amplicon with respect to d.

4. Indirect immunofluorescence with anti-centromere serum indicates that the functional centromere is located on amplicon a.

TABLE 1

| Amplicon number of λneo chromosomes in 254 days culture. | | |
|---|---|---|
| Number of amplicons | Number of Cells | % |
| 3 | 1 | 0.27 |
| 4 | 2 | 0.53 |
| 5 | 9 | 2.40 |
| 6 | 7 | 7.20 |
| 7 | 300 | 80.00 |
| 8 | 10 | 2.66 |
| 9 | 3 | 0.80 |
| 10 | 2 | 0.53 |
| 11 | 1 | 0.27 |
| 12 | 0 | 0.00 |
| 13 | 1 | 0.27 |
| translocations | 19 | 5.07 |
| Total: | 375 | 100.00 |

Hoechst dye 33258-treated KE1 2/4 metaphases were stained with carbol-fuchsin and analyzed by light microscopy. "Translocations" represents those metaphases in which either the whole λneo chromosomes or fragments of it were translocated to mouse or Chinese hamster chromosomes. In 16 metaphases out of 391, the λneo chromosome was not found.

Figure 2B:
FIG. 2B: λneo chromosomes with different amplicon numbers showing the presence of the terminal amplicons.

5. In several thousands of Hoechst dye-treated, carbol fuchsin-stained metaphases many λneo chromosomes were found that carried less or more amplicons than 7. The majority of these chromosomes contained the terminal e,f,g amplicons (FIG. 2B). Several hundreds of immunostained Hoechst 33258-treated metaphases were analyzed and not a single λneo chromosome was found showing a centromere localization other than the terminal one. These observations suggest that the extension of λneo chromosomes occurred within the chromosome arm, and not at the end of the chromosome.

Figure 2C:
FIG. 2C: λneo chromosomes showing different amplicon numbers on the sister chromatids; arrows indicate unpaired amplicons.

6. Eight out of approximately 7500 λneo chromosomes, showed unequal amplicon numbers between sister chromatids (FIG. 2C). However, in all cases the terminal amplicons were present in both chromatids.

Figure 1H:
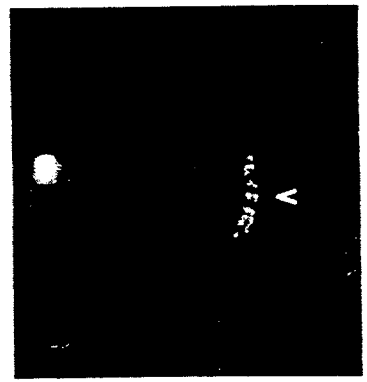
FIG. 1H: In situ hybridization of Hoechst dye 33258-treated KE1 2/4 metaphase plate with biotin-labelled human (CM8) DNA. Arrowheads indicate λneo chromosomes.

7. The in situ hybridization on Hoechst dye-treated λneo chromosomes indicated that the undercondensed regions were not labeled when human (CM8) DNA was used as the probe (FIG. 1H).

Figure 3A:
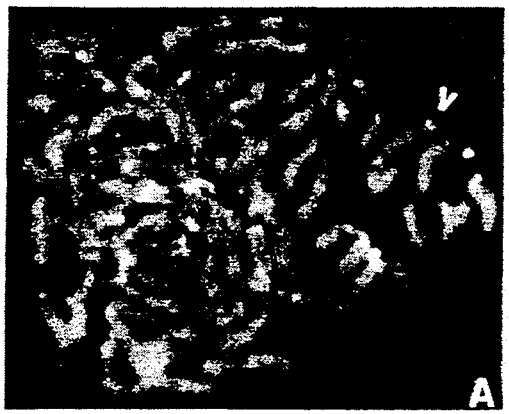
FIG. 3A: Immunostaining of Hoechst dye 33258-treated KE1 2/4 chromosomes with anti-centromere serum. The arrowhead shows the λneo chromosome with a terminal centromere.
Figure 3B:
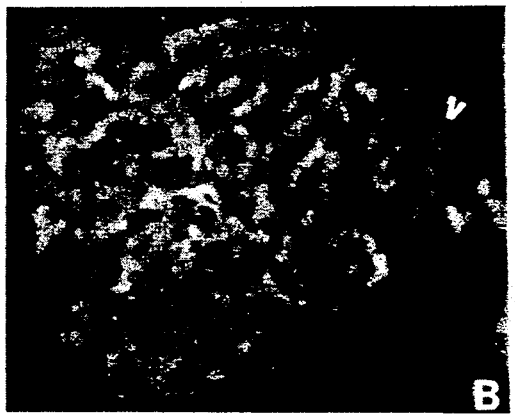
FIG. 3B: DNA staining of the same metaphase.
Figure 3C:
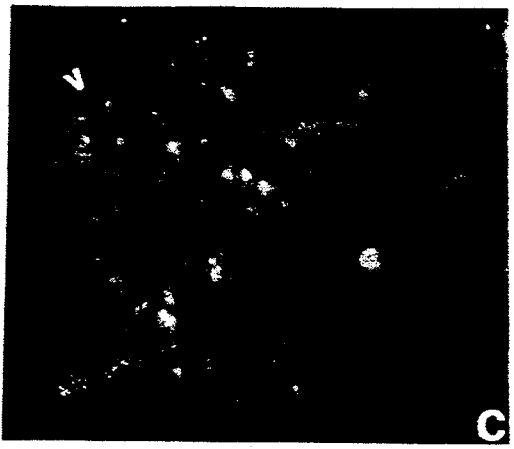
FIG. 3C: In situ hybridization of KE1 2/4 chromosomes with mouse minor satellite DNA probe, and subsequently with lambda DNA probe.
Figure 3D:
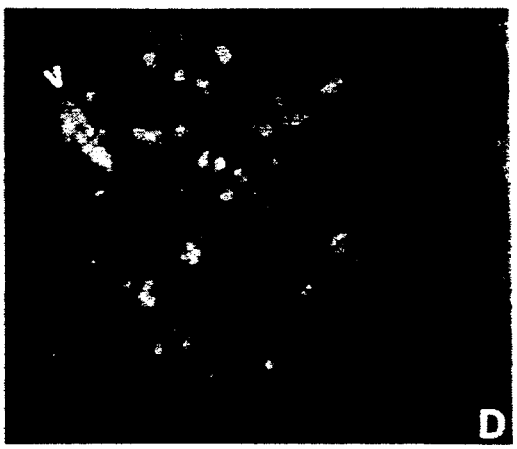
FIG. 3D: The arrowheads show λneo chromosomes.

Recently, Wong and Rattner have localized mouse minor satellite DNA specifically to the centromeres of all mouse chromosomes (Wong, et al., supra.). Using the same DNA probe, it was found that all centromeres of the chromosomes of EC3/7 cells, except the marker centromere, showed a positive hybridization signal. Similar results were obtained in KE1 2/4 cells. With the mouse centromeres an intense centromere hybridization was detected, but the centromere of the λneo chromosome was lacking any hybridization signal (FIG. 3B). To identify the λneo chromosome, "double" in situ hybridizations were performed. The same chromosome preparations were rehybridized with a λ DNA probe (FIG. 3C).

Figure 3E:
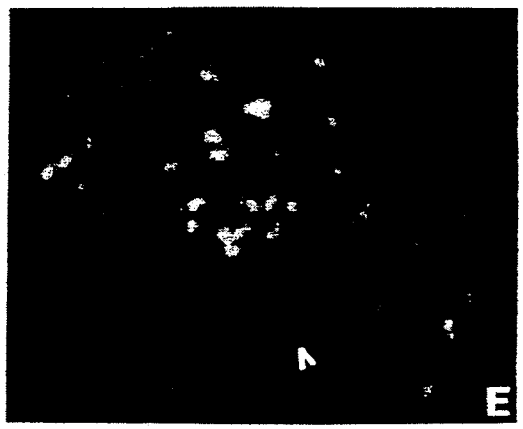
FIG. 3E: Same as Panel C, but 5 times the amount of mouse minor satellite DNA probe was used. Note the weak banded hybridization pattern of the λneo chromosome (arrowhead).
Figure 3F:
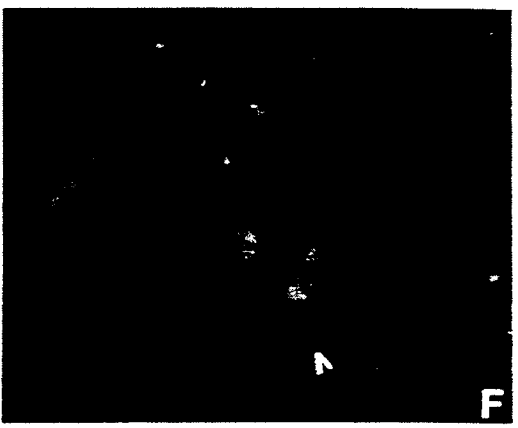
FIG. 3F: The subsequent hybridization of the same metaphase with lambda DNA probe.

Using 5 times the amount of the minor satellite DNA probe (2.8 μg/ml), a banded hybridization pattern was observed on the λneo chromosome (FIG. 3E, F), which corresponded to the localization of the mouse major satellite sequences (for a comparison see FIG. 1F). This weak hybridization signal can be attributed to a cross-hybridization of the mouse minor satellite probe and the major satellite sequences, as these sequences exhibit a significant homology in certain regions (Wong, et al., supra).

I claim:

1. A method of producing a cell line which comprises a functioning centromere comprising human DNA sequences, wherein the centromere is present on a chromosome, wherein all of the centromeres of said chromosome comprise human sequences, comprising:

fusing cells of a cell line deposited at the European Collection of Animal Cell Culture (ECACC) under accession no. 90051001 with CHO K-20 cells to form fused cell hybrids;

screening said fused cell hybrids or progeny for cells which are devoid of a dicentric chromosome but which contain a centromere which comprises human DNA.

2. A cell line made by the process of claim 1.

3. A method of producing a cell line which comprises a functioning centromere comprising human DNA sequences, wherein the centromere is present on a chromosome, wherein all of the centromeres of said chromosome comprise human sequences, comprising:

growing cells of a cell line deposited at the European Collection of Animal Cell Culture (ECACC) under accession no. 90051001 in a culture medium comprising a selective agent for an aminoglycoside-3' phosphotranferase-II gene, said selective agent present in the culture medium in an amount greater than ten times the amount which kills 50% of the cells;

selecting cell which survive in said culture medium;

screening the surviving cells or their progeny for cells which are devoid of a dicentric chromosome.

4. A cell line made by the process of claim 3.

5. A non-human cell line which comprises a functioning centromere derived from a cell line which is deposited at the European Collection of Animal Cell Cultures (ECACC) under accession no. 90051001, wherein the centromere is present on a chromosome wherein all of the centromeres of said chromosome comprise cloned human sequences.

6. The cell line of claim 5 wherein the cell line is a mouse-hamster hybrid cell line produced by fusion with CHO K-20 cells.

7. The cell line of claim 5 wherein the centromere is present on a chromosome which is the size of a full-length rodent chromosome.

8. The cell line of claim 5 wherein the centromere is present on a minichromosome which is less than half the length of the smallest chromosome in the cell line.

9. The cell line of claim 5 wherein the centromere is present on a chromosome which is stably maintained.

10. The cell line of claim 5 wherein the chromosome is stably maintained in the absence of a selective agent.

11. The cell line of claim 5 wherein the centromere is retained in at least 90% of the cells of the cell line after 150 cell generations.

12. The cell line of claim 5 wherein the centromere is retained in at least 95% of the cells of the cell line after 150 cell generations.

* * * * *